(12) United States Patent
Hill et al.

(10) Patent No.: US 10,750,975 B2
(45) Date of Patent: Aug. 25, 2020

(54) METHODS AND SYSTEMS FOR GENERATING SMOOTHED IMAGES OF AN ELONGATE MEDICAL DEVICE

(71) Applicant: St. Jude Medical, Cardiology Division, Inc., St. Paul, MN (US)

(72) Inventors: Anthony D. Hill, Minneapolis, MN (US); Yuriy Malinin, Edina, MN (US)

(73) Assignee: ST. JUDE MEDICAL, CARDIOLOGY DIVISION, INC., St. Paul, MN (US)

( * ) Notice: Subject to any disclaimer, the term of this patent is extended or adjusted under 35 U.S.C. 154(b) by 112 days.

(21) Appl. No.: 15/634,437

(22) Filed: Jun. 27, 2017

(65) Prior Publication Data

US 2018/0014751 A1    Jan. 18, 2018

Related U.S. Application Data

(60) Provisional application No. 62/362,780, filed on Jul. 15, 2016.

(51) Int. Cl.
*A61B 5/06* (2006.01)
*A61B 5/042* (2006.01)
(Continued)

(52) U.S. Cl.
CPC .............. *A61B 5/065* (2013.01); *A61B 5/042* (2013.01); *A61B 5/6858* (2013.01);
(Continued)

(58) Field of Classification Search
None
See application file for complete search history.

(56) References Cited

U.S. PATENT DOCUMENTS

| 5,729,129 | A | * | 3/1998 | Acker | ..................... A61B 5/06 324/207.12 |
| 6,233,476 | B1 | | 5/2001 | Strommer et al. | |

(Continued)

FOREIGN PATENT DOCUMENTS

| WO | 2006121740 A2 | 11/2006 |
| WO | 2010076676 A1 | 7/2010 |
| WO | 2015130824 A1 | 9/2015 |

OTHER PUBLICATIONS

Hasanzadeh et al., "Model-Based Force Estimation for Intracardiac Catheters". IEEE/ASME Transactions on Mechatronics, vol. 21, No. 1, Feb. 2016, pp. 154-162. (Year: 2016).*

*Primary Examiner* — James M Kish
(74) *Attorney, Agent, or Firm* — Armstrong Teasdale LLP

(57) ABSTRACT

The present disclosure provides systems and methods for generating smoothed images of an elongate medical device including a plurality of position sensors. The system includes a model construction system configured to be coupled to the medical device and acquire data points corresponding to positions of the position sensors. The computer-based model construction system is further configured to establish a coordinate system, calculate a coordinate for each position sensor, estimate a set of true parameters describing the medical device including a curvature term and a torsion term, calculate a measurement error for each position sensor based on a stiffness parameter, compute smoothed data points for the position sensors based on (i) a function of the estimated set of true parameters and the coordinates of the position sensors, and (ii) a weighting of the measurement error, generate an image of the medical device using the smoothed data points, and display the image.

20 Claims, 7 Drawing Sheets

(51) Int. Cl.
*A61B 5/00* (2006.01)
*A61B 18/14* (2006.01)
*A61B 18/00* (2006.01)
*A61B 34/20* (2016.01)
*A61B 34/10* (2016.01)

(52) U.S. Cl.
CPC ......... *A61B 5/6856* (2013.01); *A61B 18/1492* (2013.01); *A61B 2018/0016* (2013.01); *A61B 2018/00267* (2013.01); *A61B 2018/00357* (2013.01); *A61B 2018/00386* (2013.01); *A61B 2018/1467* (2013.01); *A61B 2034/107* (2016.02); *A61B 2034/2051* (2016.02)

(56) References Cited

U.S. PATENT DOCUMENTS

| | | | |
|---|---|---|---|
| 6,498,944 B1 | 12/2002 | Ben-Haim et al. | |
| 6,690,963 B2 | 2/2004 | Ben-Haim et al. | |
| 6,788,967 B2 | 9/2004 | Ben-Haim et al. | |
| 7,197,354 B2 | 3/2007 | Sobe | |
| 7,263,397 B2 | 8/2007 | Hauck et al. | |
| 7,386,339 B2 | 6/2008 | Strommer et al. | |
| 2008/0221438 A1* | 9/2008 | Chen | A61B 5/0422 600/424 |
| 2008/0221643 A1 | 9/2008 | Olson et al. | |
| 2012/0150022 A1* | 6/2012 | Bar-Tal | A61B 5/063 600/424 |
| 2012/0172713 A1* | 7/2012 | Carbonera | A61B 5/065 600/424 |
| 2012/0302869 A1 | 11/2012 | Koyrakh et al. | |

\* cited by examiner

METHODS AND SYSTEMS FOR GENERATING SMOOTHED IMAGES OF AN ELONGATE MEDICAL DEVICE

CROSS-REFERENCE TO RELATED APPLICATIONS

This application claims the benefit of U.S. Provisional Patent Application No. 62/362,780, filed Jul. 15, 2016, the contents of which are hereby incorporated by reference herein in their entirety.

FIELD OF THE DISCLOSURE

This disclosure relates to systems and methods for generating smoothed images of an elongate medical device. More particularly, this disclosure relates to computer-implemented systems and methods for generating smoothed images of an elongate medical device, such as, for example, a catheter within a body.

BACKGROUND

Catheters are used to perform a variety of tasks within human bodies and other bodies including the delivery of medicine and fluids, the removal of bodily fluids, and the transport of surgical tools and instruments. In the diagnosis and treatment of atrial fibrillation, for example, catheters may be used to deliver electrodes to the heart for electrophysiological mapping of the surface of the heart and to deliver ablative energy to the surface, among other tasks. In order to properly administer treatment, the position and orientation of a catheter inside the body must be continuously monitored. One known technique for determining the position and orientation of a catheter within a body is by tracking a plurality of sensors on the catheter using a position sensing and navigation system (sometimes called a location mapping system). In one exemplary system offered for sale by St. Jude Medical, Inc., under the trademark "ENSITE NAVX", the sensors comprise electrodes. Excitation of pairs of electrodes on the outer surface of the body generates electrical fields within the body. Voltage measurements on the catheter electrodes can then be used to determine the position and orientation of the catheter electrodes within a coordinate system of the position sensing and navigation system. Other exemplary position sensing and navigation systems include magnetic systems.

In order to provide information to clinicians about the position and orientation of the catheter, the determined position and orientation of the catheter sensors is often used to render an image of the catheter relative to surrounding tissues, including heart tissues. One drawback to conventional systems, however, is that the determined position and orientation of the catheter sensors is subject to systematic errors due to subtle differences in, e.g., sensor impedances and amplifier channels. These errors can distort the rendered shape of the catheter from its true mechanical shape in the resulting image.

Moreover, certain smoothing algorithms may not be suitable for circular or otherwise curved catheters. For example, smoothing algorithms that apply basis functions to model measured electrode positions as deviations from a straight line may not appropriately model catheters having substantial curvature. Implementing such smoothing algorithms on catheters having substantial curvature may induce errors such as a reduction in a diameter in the imaged catheter.

BRIEF SUMMARY OF THE DISCLOSURE

In one embodiment, the present disclosure is directed to a system for generating an image of an elongate medical device that includes a plurality of position sensors within a body. The system includes a computer-based model construction system configured to be coupled to the elongate medical device and configured to acquire a set of measured data points corresponding to respective positions of the plurality of position sensors. The model construction system is further configured to establish a coordinate system associated with the elongate medical device, and calculate a respective coordinate in the coordinate system for each of the plurality of position sensors. The model construction system is also configured to estimate a set of true parameters describing the elongate medical device, the set of true parameters including a curvature term and a torsion term, and calculate a measurement error for each of the plurality of position sensors based at least on part on a respective stiffness parameter. The model construction system is still further configured to compute smoothed data points for the plurality of position sensors based on (i) a function of the estimated set of true parameters and the respective coordinates of each of the plurality of position sensors, and (ii) a weighting of the measurement error. The model construction system is also configured to generate an image of the elongate medical device using the smoothed data points, and display the generated image.

In another embodiment, the present disclosure is directed to a computer-implemented method of generating an image of an elongate medical device that includes a plurality of position sensors within a body. The method includes acquiring a set of measured data points corresponding to respective positions of the plurality of position sensors, establishing a coordinate system associated with the elongate medical device, and calculating a respective coordinate in the coordinate system for each of the plurality of position sensors. The method also includes estimating a set of true parameters describing the elongate medical device, the set of true parameters including a curvature term and a torsion term, and calculating a measurement error for each of the plurality of position sensors based at least in part on a respective stiffness parameter. The method still further includes computing smoothed data points for the plurality of position sensors based on (i) a function of the estimated set of true parameters and the respective coordinates of each of the plurality of position sensors, and (ii) a weighting of the measurement error. The method also includes generating an image of the elongate medical device using the smoothed data points, and displaying the generated image.

In another embodiment, the present disclosure is directed to a processing apparatus for generating an image of an elongate medical device that includes a plurality of position sensors within a body. The processing apparatus is configured to acquire a set of measured data points corresponding to respective positions of the plurality of position sensors, establish a coordinate system associated with the elongate medical device, and calculate a respective coordinate in the coordinate system for each of the plurality of position sensors. The processing apparatus is also configured to estimate a set of true parameters describing the elongate medical device, the set of true parameters including a curvature term and a torsion term, and calculate a measurement error for each of the plurality of position sensors based at least on part on a respective stiffness parameter. The processing apparatus is further configured to compute smoothed data points for the plurality of position sensors based on (i) a function of the estimated set of true parameters and the respective coordinates of each of the plurality of position sensors, and (ii) a weighting of the measurement error. The processing apparatus is still further configured to generate an image of the elongate medical device using the smoothed data points, and display the generated image.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

The disclosure provides systems and methods for generating a smoothed image of an elongate medical device (e.g., a catheter) within a body. In particular, the systems and methods described herein are suitable for generating images of curved or circular elongate medical devices by describing positions of position sensors (e.g., electrodes) on the elongate medical device as deviations from a curved parametric form. Accordingly, the systems and methods described herein can be used to image one-dimensional medical devices as well as two-dimensional medical devices, such as planar catheters.

More specifically, the system described herein includes a model construction system configured to implement a smoothing algorithm. The smoothing algorithm represents an improvement over previous algorithms by changing the basis functions to those that assume measured positions of position sensors are explained as deviations from a curve in space, rather than from a straight line. This approach applies equally to straight medical devices (as straight lines are curves with a zero curvature) and to medical devices with substantial curvature. This approach is beneficial for any set of position sensors on a curved medical device, including linear mapping catheters which are looped around a chamber, such as in atrial flutter and ventricular mapping procedures.

Where the term "planar" or, similarly, "plane" is used herein, it should be understood to refer to a topological plane. In other words, a "plane" may not be "flat" in a Cartesian coordinate system, but rather represents a two-dimensional manifold that is planar in a topological sense.

Figure 1:
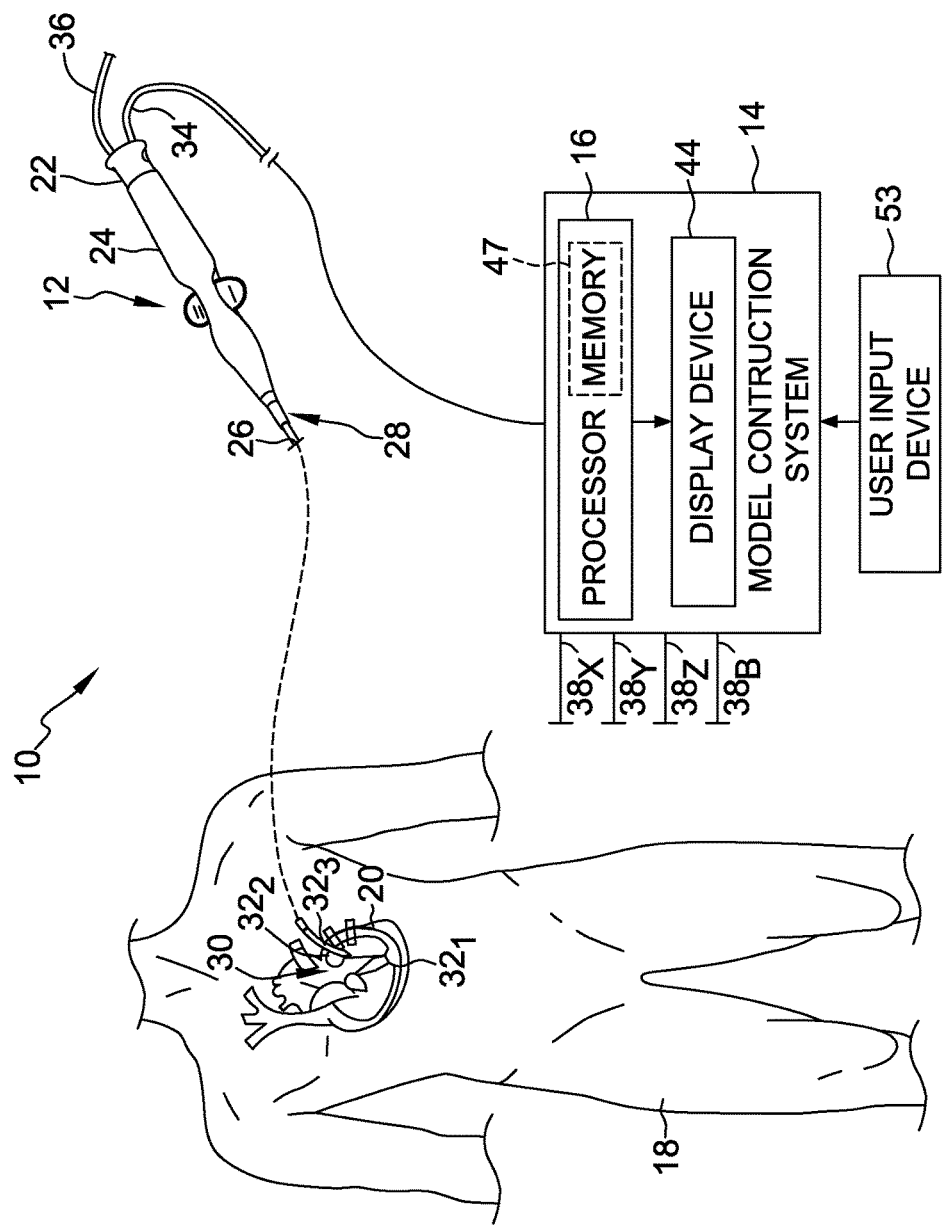
FIG. 1 is a diagrammatic view of a system for generating smooth images of an elongate medical device according to one embodiment.

Referring now to the drawings wherein like reference numerals are used to identify identical components in the various views, FIG. 1 illustrates one exemplary embodiment of a system 10 for generating a smoothed image of an elongate medical device within a body. In this embodiment, the system 10 includes, among other components, an elongate medical device and a model construction system 14. In this embodiment, the elongate medical device is a catheter 12, and model construction system 14 includes, in part, a processing apparatus 16. Processing apparatus 16 may take the form of an electronic control unit, for example, that is configured to generate and render a smooth image of catheter 12. Although the system is described in terms of rendering a catheter, it should be understood that various elongate medical devices (e.g., introducer sheaths, pacing leads, etc.) could be rendered using the inventive system.

As illustrated in FIG. 1, catheter 12 is configured to be inserted into a patient's body 18, and more particularly, into the patient's heart 20. Catheter 12 may include a cable connector or interface 22, a handle 24, a shaft 26 having a proximal end 28 and a distal end 30 (as used herein, "proximal" refers to a direction toward the portion of the catheter 12 near the clinician, and "distal" refers to a direction away from the clinician and (generally) inside the body of a patient). Catheter 12 may comprise an electrophysiological (EP) catheter for use in gathering EP data associated with the heart 20 to enable generation of an image of the geometry of the heart surface and related EP data. Catheter 12 may also allow removal of bodily fluids or injection of fluids and medicine into the body and may further provide a means for transporting surgical tools or instruments within a body including those used for pacing or tissue ablation. Although catheter 12 comprises an EP catheter in the illustrated embodiment, it should be understood that the inventive system can be used to visually render a variety of different types of catheters including, for example, intracardiac echocardiography (ICE) catheters and ablation catheters using a wide variety of ablative energies (e.g., radio-frequency, cryogenic, ultrasound, laser or other light, etc.). Catheter 12 may be formed from conventional materials such as polyurethane.

Figure 2:
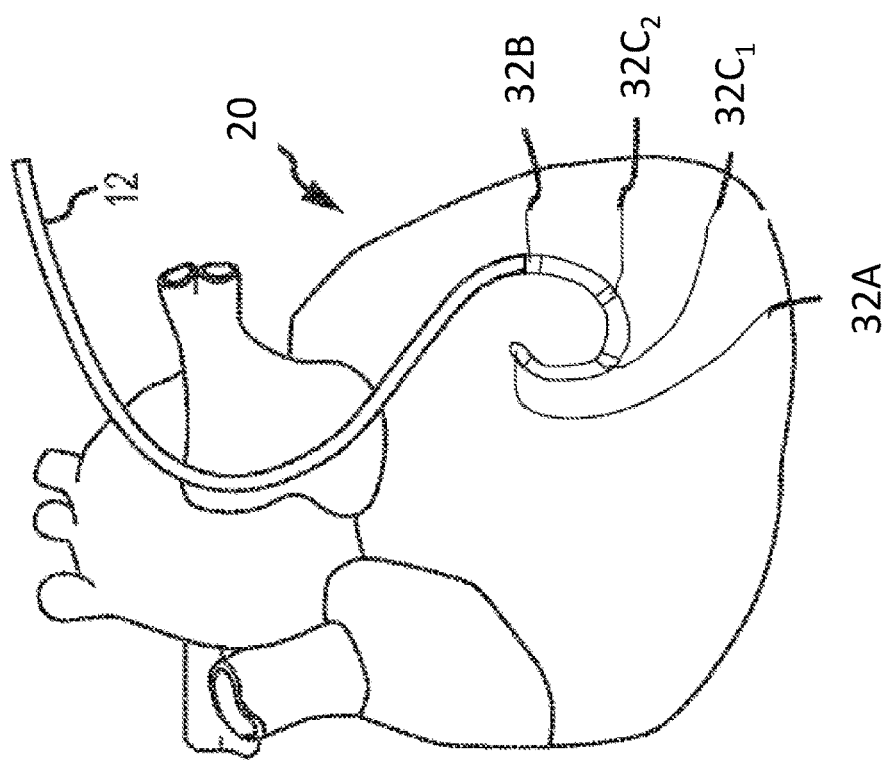
FIG. 2 is a diagrammatic view of the distal end of a catheter used in the system shown in FIG. 1 within a human heart.

Referring to FIG. 2, catheter 12 may include a plurality of EP mapping electrodes 32 such as distal tip electrode 32A, proximal ring electrode 32B, and intermediate ring electrodes 32C. Electrodes 32 are provided to generate information regarding the position of catheter 12 and therefore may function as position sensors in accordance with the present invention. Electrodes 32 also provide information regarding the geometry of heart 20 and other EP data as discussed in greater detail hereinbelow. Catheter 12 may further include other conventional components such as, for example and without limitation, a temperature sensor, additional sensors or electrodes, ablation elements (e.g., ablation tip electrodes for delivering RF ablative energy, high intensity focused ultrasound ablation elements, etc.), and corresponding conductors or leads.

Connector 22 provides mechanical, fluid, and electrical connection(s) for cables, such as, for example, cables 34, 36 extending to model construction system 14 and/or other components of system 10 (e.g., a visualization, navigation, and/or mapping system (if separate and distinct from model construction system 14), an ablation generator, irrigation source, etc.). Connector 22 is conventional in the art and is disposed at proximal end 28 of catheter 12, and handle 24 thereof, in particular.

Handle 24, which is disposed at proximal end 28 of shaft 26, provides a location for the clinician to hold catheter 12 and may further provide means for steering or guiding shaft 26 within body 18 of the patient. For example, handle 24 may include means to change the length of a steering wire extending through catheter 12 to distal end 30 of shaft 26 to steer shaft 26. Handle 24 is also conventional in the art and it will be understood that the construction of handle 24 may vary. In other embodiments, catheter 12 may be robotically driven or controlled. Accordingly, rather than a clinician manipulating a handle to steer or guide catheter 12 and shaft 26 thereof, in such an embodiments, a robot is used to manipulate catheter 12.

Shaft 26 is an elongate, tubular, flexible member configured for movement within body 18. Shaft 26 supports, for example and without limitation, sensors and/or electrodes mounted thereon, such as, for example, sensors 32, associated conductors, and possibly additional electronics used for signal processing and conditioning. Shaft 26 may also permit transport, delivery, and/or removal of fluids (including irrigation fluids, cryogenic ablation fluids, and bodily fluids), medicines, and/or surgical tools or instruments. Shaft 26 may be made from conventional materials such as polyurethane, and defines one or more lumens configured to house and/or transport electrical conductors, fluids, or surgical tools. Shaft 26 may be introduced into a blood vessel or other structure within the body 18 through a conventional introducer. Shaft 26 may then be steered or guided through body 18 to a desired location, such as heart 20, using means well known in the art.

Figure 3:
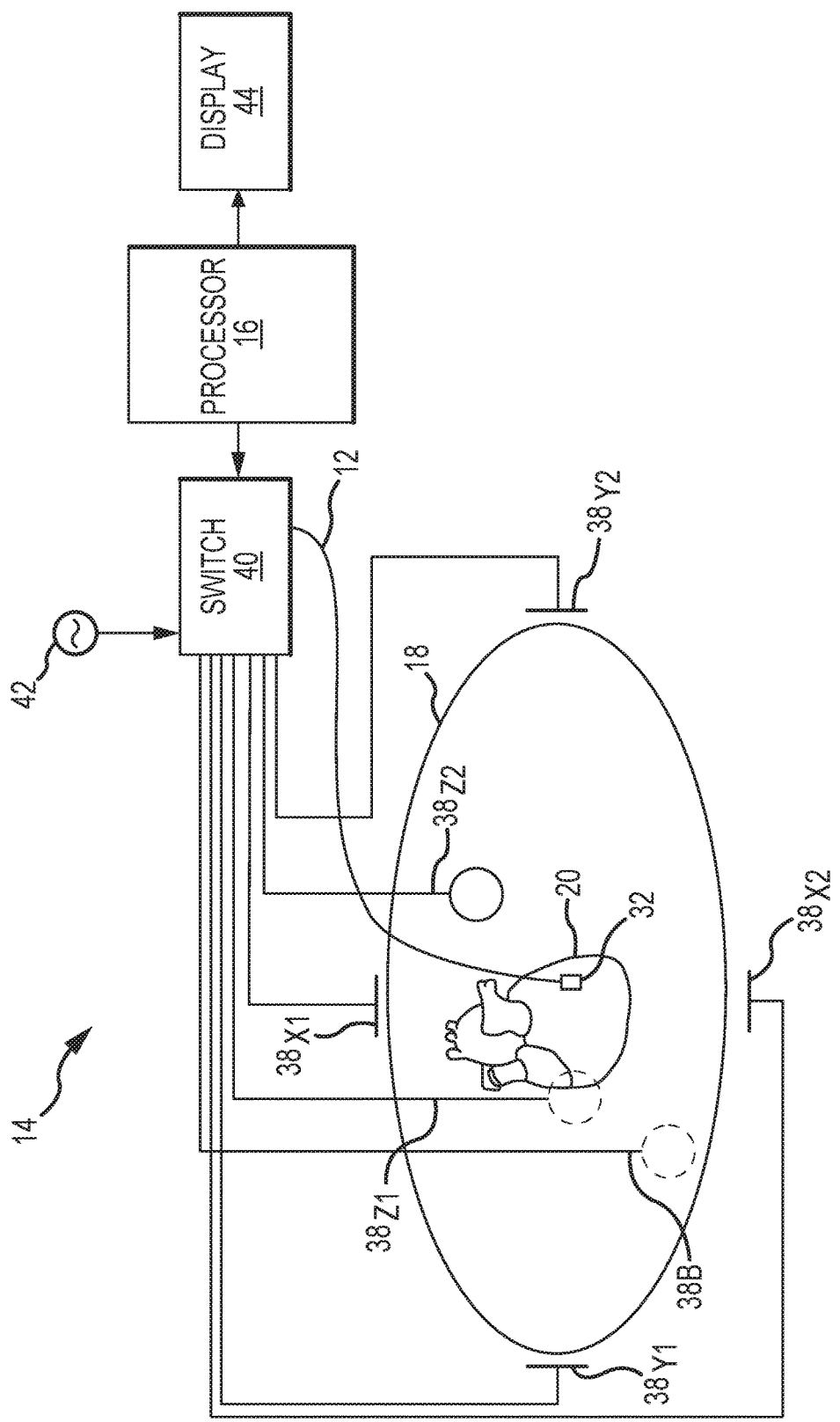
FIG. 3 is a diagrammatic and schematic view of a model construction system of the system illustrated in FIG. 1.

With reference to FIG. 3, in addition to the processing apparatus 16, model construction system 14 may include, among other possible components, a plurality of patch electrodes 38, a multiplex switch 40, a signal generator 42, and a display device 44. In other embodiments, some or all of these components are separate and distinct from model construction system 14 but are electrically connected to, and configured for communication with, model construction system 14.

Processing apparatus 16 may include a programmable microprocessor or microcontroller, or may include an application specific integrated circuit (ASIC). Processing apparatus 16 may include a central processing unit (CPU) and an input/output (I/O) interface through which the processing apparatus 16 may receive a plurality of input signals including, for example, signals generated by patch electrodes 38 and position sensors 32, and generate a plurality of output signals including, for example, those used to control and/or provide data to, for example, display device 44 and switch 40. Processing apparatus 16 may be configured to perform various functions, such as those described in greater detail above and below, with appropriate programming instructions or code (i.e., software). Accordingly, processing apparatus 16 is programmed with one or more computer programs encoded on a computer storage medium for performing the functionality described herein.

With the possible exception of patch electrode $38_B$ called a "belly patch," patch electrodes 38 are provided to generate electrical signals used, for example, in determining the position and orientation of catheter 12 within a three dimensional coordinate system and in generating EP data regarding heart 20. In one embodiment, patch electrodes 38 are placed orthogonally on the surface of body 18 and are used to create axes-specific electric fields within body 18. For instance, in one embodiment, patch electrodes $38_{X1}$, $38_{X2}$ may be placed along a first (x) axis. Patch electrodes $38_{Y1}$, $38_{Y2}$ may be placed along a second (y) axis, and patch electrodes $38_{Z1}$, $38_{Z2}$ may be placed along a third (z) axis. In addition, a reference electrode (not shown) may also be attached to body 18. Each of patch electrodes 38 may be coupled to multiplex switch 40. In this embodiment, processing apparatus 16 is configured, through appropriate software, to provide control signals to switch 40 to thereby sequentially couple pairs of electrodes 38 to signal generator 42. Excitation of each pair of electrodes 38 generates an electric field within body 18 and within an area of interest such as heart 20. Voltage levels at non-excited electrodes 38, which are referenced to belly patch $38_B$, are filtered and converted and provided to processing apparatus 16 for use as reference values.

Electrodes 32 on catheter 12 are disposed within electrical fields created in body 18 (e.g., within the heart 20) by exciting patch electrodes 38. Electrodes 32 experience voltages that are dependent on the location between the patch electrodes 38 and the position of the electrodes 32 relative to the surface of the heart 20. Voltage measurement comparisons made between electrodes 32 can be used to determine the position of the electrodes 32 within heart 20. Movement of the electrodes 32 within heart 20 (e.g., within a heart chamber) produces information regarding the geometry of the heart 20 as well as EP data.

As briefly described above, and as will be described in greater detail below, model construction system 14 is provided to determine the position and orientation of position sensors such as electrodes 32 on an elongate medical device such as catheter 12. Model construction system 14 is configured to use this position and orientation data to generate a smoothed image of catheter 12 within heart 20. More particularly, processing apparatus 16 of model construction system 14 is configured to acquire measured data points collected using position sensors 32 (i.e., electrodes 32), the measured data points corresponding to respective position of electrodes 32. In this embodiment, model construction system 14 acquires the measured data points by activating electrodes 32 as described above. In other embodiments, however, model construction system 14 may simply acquire the measured data points from electrodes 32 or another component in system 10, such as, for example, a memory or other storage device that is part of model construction system 14 or accessible thereby, without affirmatively taking part in the collection of the measured data points. Model construction system 14 is configured to describe the measured data points as deviations from a parametric form (e.g., a curve, in the case of a one-dimensional catheter 12, or a plane, in the case of a two-dimensional catheter 12) and generate a smoothed image of the catheter using such deviations. For purposes of illustration and clarity, the description below will be limited to an embodiment wherein model construction system 14 is configured to both generate the image and also acquire the measured data points by functioning with electrodes 32 in the collection of the measured data points. It will be appreciated, however, that other embodiments wherein model construction system 14 only acquires measured data point from electrodes 32 or another component of system 10 and then generate a smoothed image based thereon remain within the spirit and scope of the present disclosure.

Accordingly, in this embodiment, in addition to generating a smoothed image of catheter 12, model construction system 14 is configured to function with electrodes 32 to collect data points that are used in the modelling of catheter 12. Model construction system 14 may comprise an electric field-based system, such as, for example, the EnSite™ Velocity™ system commercially available from St. Jude Medical, Inc., and generally shown with reference to U.S. Pat. No. 7,263,397 entitled "Method and Apparatus for Catheter Navigation and Location and Mapping in the Heart", the entire disclosure of which is incorporated herein by reference. In other embodiments, however, model construction system 14 may comprise other types of systems, such as, for example and without limitation: a magnetic-field based system such as the Carto™ system available from Biosense Webster, and as generally shown with reference to one or more of U.S. Pat. No. 6,498,944 entitled "Intrabody Measurement," U.S. Pat. No. 6,788,967 entitled "Medical Diagnosis, Treatment and Imaging Systems," and U.S. Pat. No. 6,690,963 entitled "System and Method for Determining the Location and Orientation of an Invasive Medical Instrument," the entire disclosures of which are incorporated herein by reference, or the gMPS system from MediGuide Ltd., and as generally shown with reference to one or more of U.S. Pat. No. 6,233,476 entitled "Medical Positioning System," U.S. Pat. No. 7,197,354 entitled "System for Determining the Position and Orientation of a Catheter," and U.S. Pat. No. 7,386,339 entitled "Medical Imaging and Navigation System," the entire disclosures of which are incorporated herein by reference; a combination electric field-based and magnetic field-based system such as the Carto 3™ System also available from Biosense Webster; as well as other impedance-based localization systems, acoustic or ultrasound-based systems, and commonly available fluoroscopic, computed tomography (CT), and magnetic resonance imaging (MRI)-based systems.

As briefly described above, position sensor(s) 32 produce signals indicative of catheter location (position and/or orientation) information. In this embodiment, wherein model construction system 14 is an electric field-based system, position sensors 32 comprise electrodes. Alternatively, in an embodiment where model construction system 14 is a magnetic field-based system, position sensors 32 may include one or more magnetic sensors configured to detect one or more characteristics of a low-strength magnetic field. For instance, in one exemplary embodiment, position sensors 32 may include magnetic coils disposed on or in shaft 26 of catheter 12.

For purposes of clarity and illustration, model construction system 14 will hereinafter be described as including an electric field-based system, such as, for example, the EnSite™ Velocity™ system identified above. It will be appreciated that while the description below is primarily limited to an embodiment wherein position sensors 32 include electrodes, in other embodiments, position sensors 32 may include one or more magnetic field sensors (e.g., coils). Accordingly, model construction systems that include positioning sensor(s) other than the sensors or electrodes described below remain within the spirit and scope of the present disclosure.

In this embodiment, electrodes 32 of catheter 12 are electrically coupled to processing apparatus 16 and are configured to serve a position sensing function. More particularly, electrodes 32 are placed within electric fields created in body 18 (e.g., within the heart) by exciting patch electrodes 38. Using various known algorithms, the processing apparatus 16 may then determine the location (position and orientation) of each electrode 32 and record it as a measured data point corresponding to a respective position of each electrode 32 in a memory or storage device, such as memory 47, associated with or accessible by processing apparatus 16. In some embodiments, prior to recording the measured data point, raw measured data represented by the signals received by processing apparatus 16 may be corrected by processing apparatus 16 to account for respiration, cardiac activity, and other artifacts using known or hereafter developed techniques.

While the description above has thus far been generally with respect to an orthogonal arrangement of patch electrodes 38, the present disclosure is not meant to be so limited. Rather, in other embodiments, non-orthogonal arrangements (e.g., arrangements of non-orthogonal dipoles) may be used to determine the location coordinates of sensor 32. In another exemplary embodiment, multiple patch electrodes 38 may be arranged linearly along a common axis. In such an embodiment, excitation of an electrode pair comprising one of patch electrodes 38 and a first electrode 32 mounted on catheter 12 generates an electric field. The non-excited patch electrodes 38 may then measure potentials that can be used to determine the position of another electrode 32. Accordingly, in such an embodiment, the excitation of multiple electrode pairs comprising different patch electrodes 38 and the first catheter-mounted electrode 32 may be used to determine the position of another 32.

Figure 4:
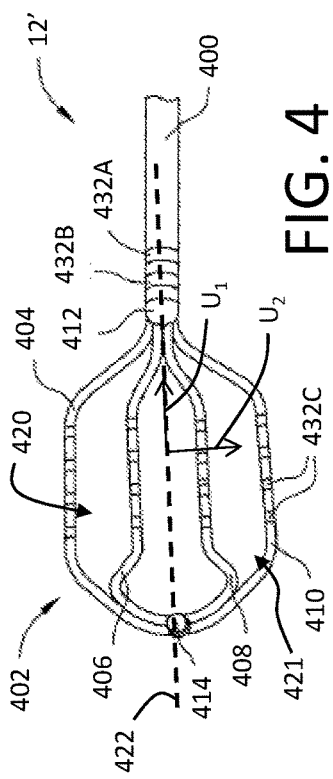
FIG. 4 is an example of a planar catheter usable with the system illustrated in FIG. 1.

FIG. 4 illustrates one embodiment of a planar catheter 12' that may be used with the system 10 shown in FIG. 1. Catheter 12' comprises a catheter body 400 coupled to a paddle 402. Catheter body 400 can further comprise a first body electrode 432A and a second body electrode 432B. Paddle 402 can comprise a first spline 404, a second spline 406, a third spline 408, and a fourth spline 410 that are coupled to catheter body 400 by a proximal coupler 412 and coupled to each other by a distal connector 414 at a distal end of paddle 402. In one embodiment, first spline 404 and fourth spline 410 can be one continuous segment, and second spline 406 and third spline 408 can be another continuous segment. In other embodiments the various splines can be separate segments coupled to each other. The plurality of splines can further comprise a varying number of electrodes 432C. The electrodes in the illustrated embodiment can comprise ring electrodes evenly spaced along the splines. In other embodiments the electrodes can be evenly or unevenly spaced and the electrodes can comprise point or other types of electrodes.

First spline 404, second spline 406, third spline 408, and fourth spline 410 generally line in the same (topological) plane, generally indicated at 420. In other words, plane 420 is defined by a surface 421 of paddle 402 of catheter 12'. Plane 420 includes a central axis 422. Although plane 420 is illustrated as relatively flat in FIG. 4, it should be understood that paddle 402 may bend, curl, buckle, twist, and/or otherwise deform. Accordingly, plane 420 defined by paddle 420 may correspondingly deform, such that plane 420 is a non-flat topological plane. As discussed further herein, the positions of electrodes 432 may be described using a distance along a direction $U_1$, a distal-to-proximal direction along central axis 422, and a direction $U_2$, a direction from first spline 404 towards fourth spline 410.

Figure 5:
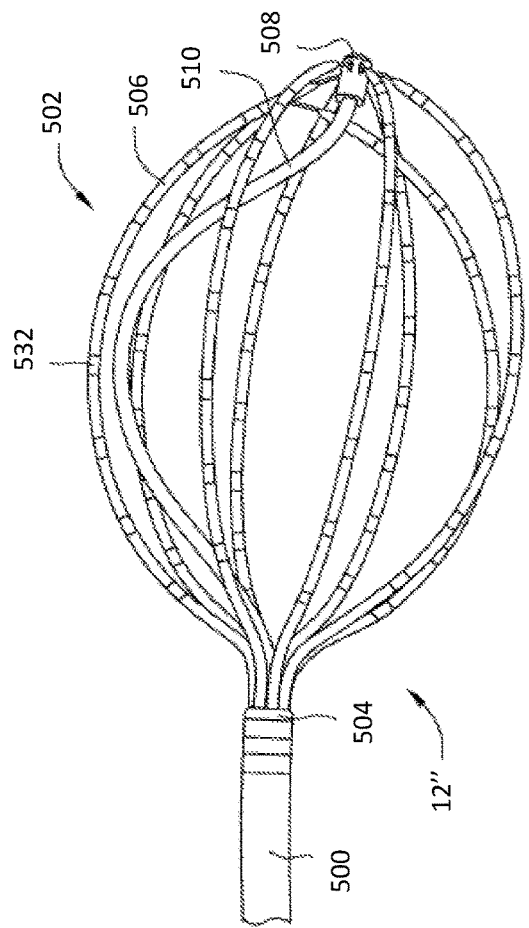
FIG. 5 is an example of a basket catheter usable with the system illustrated in FIG. 1.

FIG. 5 illustrates an embodiment of a basket catheter 12", which can be considered to be a 2D array of electrodes distributed over an ellipsoid surface, that may be used with the system 10 shown in FIG. 1. Basket catheter 12" can comprise a catheter body 500 coupled to a basket 502. Basket 502 can be coupled to catheter body 500 with a proximal connector 504. Basket 502 can comprise a plurality of splines 506, a distal coupler 508, and an irrigation tubing 510. Each of the plurality of splines 506 can comprise at least one electrode 532. In the illustrated embodiment, each of the plurality of splines comprises eight electrodes 532. However, the exact number of electrodes can be varied based on the desired characteristics.

Figure 6:
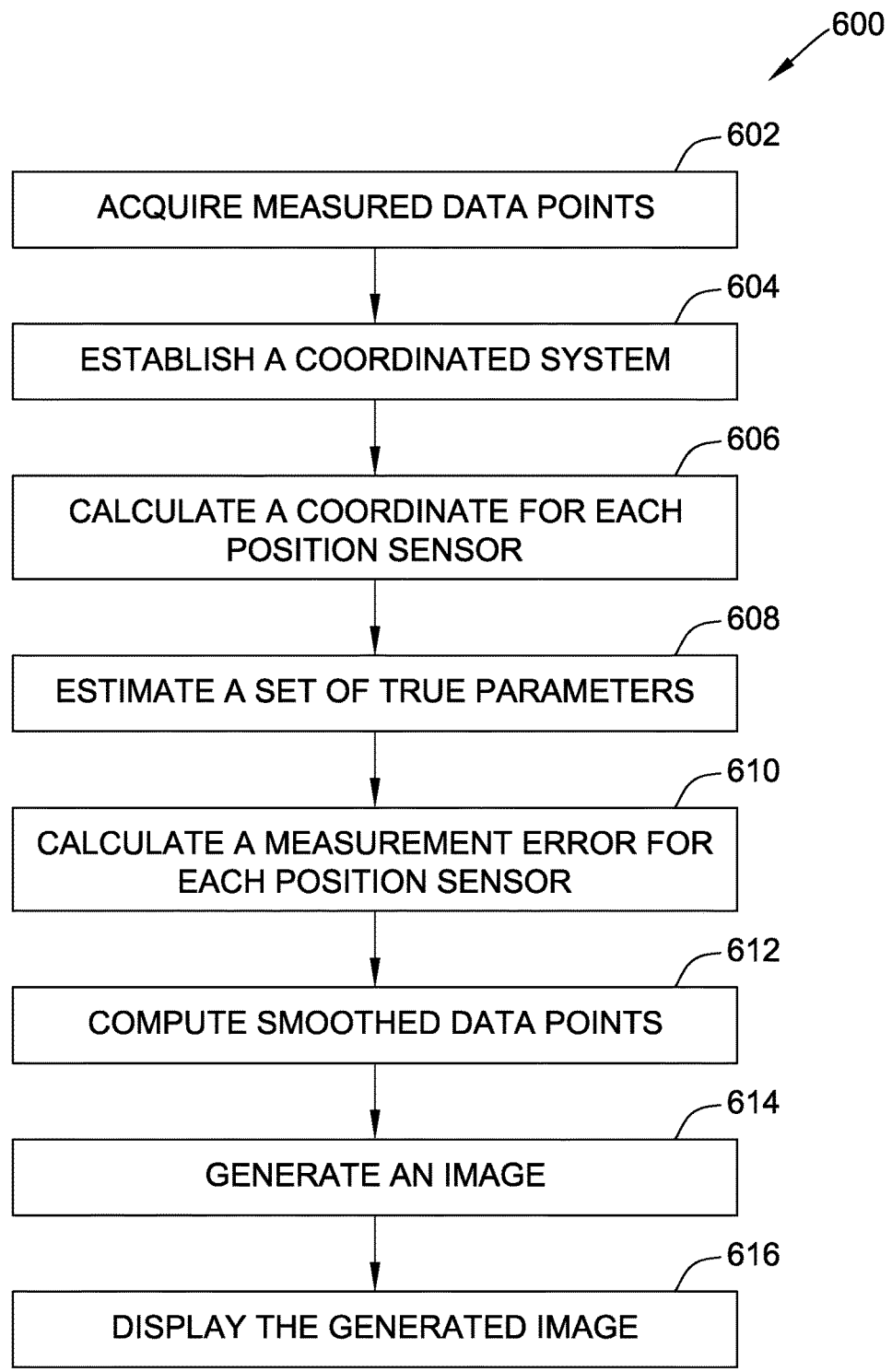
FIG. 6 is a flow chart illustrating a method for generating smooth images of an elongate medical device according to one embodiment.

Referring to FIG. 6, a method for generating a smoothed image of an elongate medical device (e.g., catheter 12) in a body (e.g., body 18) is illustrated. The method may be implemented in model construction system 14 (e.g., in processing apparatus 16), for example, as software that configures model construction system 14 to perform the steps of the method.

In a first step 602, measured data points corresponding to measured positions of each electrode 32 on catheter 12 are acquired. Electrode position measurements, like any measurement, may be expressed as a true position plus measurement error:

$$X = \langle X \rangle + \varepsilon$$

where X represents the measured position of an electrode 32 on catheter 12, $\langle X \rangle$ represents a true position of the electrode 32, and E represents the measurement error in the measured position, or the deviation from an idealized or true parametric form. If the error has zero mean over time, then temporal filtering may be used to remove the error. For catheter positions determined by measuring impedance values, such as in the EnSite™ Velocity™ system, there may be substantial electrode-specific errors that remain after temporal filtering. These remaining errors may be due to variations in manufacturing, local changes in the electrode-electrolyte interface, and/or uncompensated channel-to-channel variation in the instrumentation, among many other potential sources.

Measured positions of other points on the same catheter 12, such as measured positons of other electrodes 32, can be used to reduce the remaining error in measured electrode positions. Though the true position, orientation, and/or shape of catheter 12 on which electrodes 32 are disposed are not known, these may be inferred from a collection of the measured positions of electrodes 32 on catheter 12. Generally, a "parameterized catheter 12" may refer to a catheter 12 for which a set of parameters (e.g., position, orientation, shape, length, number of electrodes 32, distance between adjacent electrodes 32, etc.) determine the true position of an electrode 32.

In step 604, a coordinate system associated with catheter 12 (a "catheter coordinate system") is established. The individual electrode measurement errors can then be described as deviations from the true positions, as determined by the parameterized catheter and an inferred estimate of the true parameters, assuming that the measurement errors for each electrode 32 are independent and normally distributed. The true parameters are estimated or inferred to be those parameters that minimize a sum of squared measurement errors between the parametrized position and the measured positions.

$$\langle X_i \rangle = f(\langle p \rangle, U_i)$$

where $\langle X_i \rangle$ represents the true position of electrode i, $\langle p \rangle$ represents a set of true parameters, and $U_i$ represents a coordinate in the catheter coordinate system for electrode i.

In step 606, coordinate $U_i$ for each electrode 32 is calculated. For curved or linear one-dimensional catheters 12, $U_i$ is a scalar representing an arclength between the distal-most electrode (e.g., electrode 32A) and electrode i along shaft 26 of catheter 12, and p is composed of a curve parameter and an affine transformation: $\{\theta, M\}$. The parametric form of catheter 12 can be described using the following:

$$f(p, U_i) = [1\ U_i \cos(\theta U_i) \sin(\theta U_i)] M$$

This function defines the possible domain in which true positions of electrodes 32 may lie. For curved or linear one-dimensional catheters, the true positions are described by a single curve of constant curvature, such that the true position of each electrode must fit a curve defined by curve parameter θ and affine projection M.

For an exemplary planar catheter 12' (see FIG. 4), $U_i$ is a two-dimensional coordinate in plane 420 defined by surface 421 of catheter 12'. A first term ($U_{i,1}$) specifies a distance in the distal to proximal direction $U_i$ along central axis 422 of catheter 12', and a second term ($U_{i,2}$) specifies a distance from central axis 422 perpendicular to central axis 422, for example, direction $U_2$. In addition, p is composed of a curvature term, a torsion term, and an affine transformation: $\{\kappa, \tau, M\}$. κ and τ are constants over the plane defined by the surface of the catheter 12'. Moreover, $$\theta^2 = \kappa^2 + \tau^2$$

such that the curve parameter is defined by the curvature term κ and the torsion term τ.

$$\mathcal{L}_{i,1} = \frac{U_{i,1}}{\sqrt{1 + \tau^2 U_{i,2}^2}}$$

$$\mathcal{L}_{i,2} = U_{i,2} - \frac{\kappa}{\theta^2}$$

Each $\mathcal{L}$ term represents a correction in the distance measurements $U_{i,1}$, $U_{i,2}$ to account for any change in length that results from any curvature or twist (torsion) in the parametric plane defining catheter 12'.

$$f(p, U_i) = [1\ \mathcal{L}_{i,1}\ \mathcal{L}_{i,2} \cos(\theta \mathcal{L}_{i,1})\ \mathcal{L}_{i,2} \sin(\theta \mathcal{L}_{i,1})] M$$

This function defines the possible domain in which true positions of electrodes 32 may lie. For two-dimensional catheters, the true positions are described by an exemplary two-dimensional parametric form including curvature (κ) and torsion (τ) terms.

In step 608, an estimate of the true parameters, $\hat{p}$, is computed as a non-linear least-squares solution to the original measurements. Solvers such as Levenberg-Marquardt may be used for this purpose.

For all parameterized models, the measurement error ε is described by a thin-plate spline in the dimensionality of $U_i$, with a per-electrode stiffness specified by $\lambda_i$. "Stiffness" may be further described as a parameter that defines how much variation in the measured position of each electrode 32 is permitted. In other words, the larger the stiffness λ, the closer a smoothed position of that electrode 32 to the position corresponding to the inferred parameters ($U_i$). Shown below, the deviation of the smoothed positions from the measured positions (Λ) is a product of the stiffness and the difference between the measured positions and the positions resulting from the inferred parameters. In step 610, a measurement error for each electrode 32 (i.e., the measurement error in the measured position of each electrode 32) is calculated, based at least in part on stiffness parameter $\lambda_i$.

$$\varepsilon = (\Psi - \Lambda) W$$

$$\Psi_{ij} = \psi(|U_i - U_j|)$$

$$\Lambda_{ij} = \lambda_i \delta_{ij}$$

Typically, the radial basis function is defined as $\psi = r^3$ if $U_i$ is 1-D, $\psi(r) = r^2 \ln r$ if $U_i$ is 2-D and $\psi(r) = r$ if $U_i$ is 3-D. These radial basis functions are standard for thin plate splines.

These are the functions for which $\nabla^4\psi=0$ over the entire domain. This form describes biharmonic functions. Biharmonic functions describe the physics of many continua including elastostatics or Stokes flows. In the thin plate spline formulation, the biharmonic function describes the bending of an isotropic body in which all the forces on the body sum to zero. In this sense, it is smooth. This physical description leads to the description of smoothing the errors.

For a given set of stiffness parameters $\lambda_i$, and an estimate of the true parameters, $\hat{p}$, $\lambda$, the weights, W, are uniquely determined by solving the following equation (Equation (A)):

$$(\Psi-\Lambda)W=X-f(\hat{p},U_i) \quad (A)$$

In step 612, smoothed data points, $X_S$, are then computed based on (i) a function of the estimated set of true parameters—as estimated in step 608—and the respective coordinates of each of electrode 33—as calculated in step 606—as well as (ii) a smoothed fraction of the measurement error (i.e., $\Psi W$). More particularly, $X_S$ are calculated as follows:

$$X_S=f(\hat{p},U_i)+\Psi W$$

In step 614, an image (e.g., image 850, shown in FIG. 8B) is generated based on smoothed data points $X_S$. In step 616, the generated image is displayed (e.g., on display device 44, shown in FIG. 1).

Figure 7C:
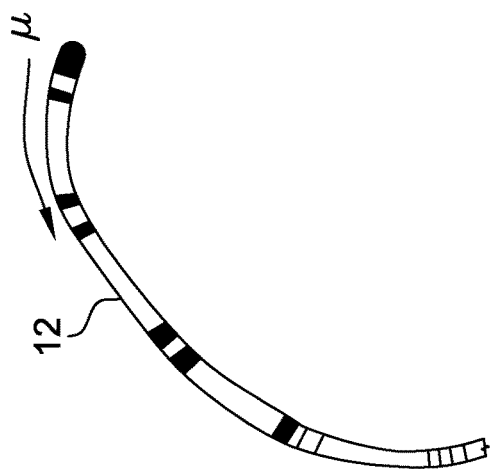
FIGS. 7A-7C illustrate example parametrization of alternative embodiments of elongate medical devices, such as catheters, used with the system shown in FIG. 1.
Figure 7B:
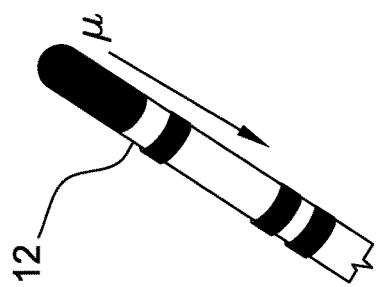
Figure 7A:
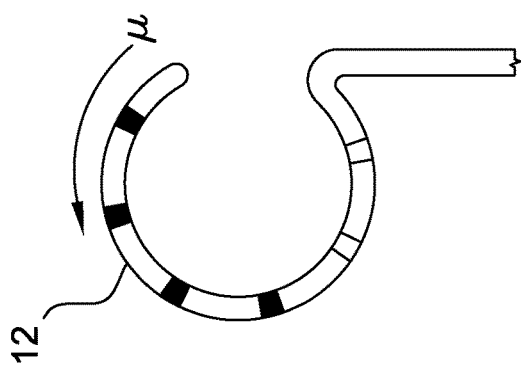

FIGS. 7A-7C illustrate example parametrization of alternative embodiments of elongate medical devices, such as catheters, used with system 10 shown in FIG. 1. Each catheter is described by different values of parameters input to a parametric form u. More specifically, FIG. 7A illustrates a parametrization u of a catheter 12 having a generally circular shape; FIG. 7B illustrates a parametrization u of a linear catheter 12; and FIG. 7C illustrates a parametrization u of a curved catheter 12 (i.e., with a lower curvature than the circular catheter 12 shown in FIG. 7A).

Figure 8B:
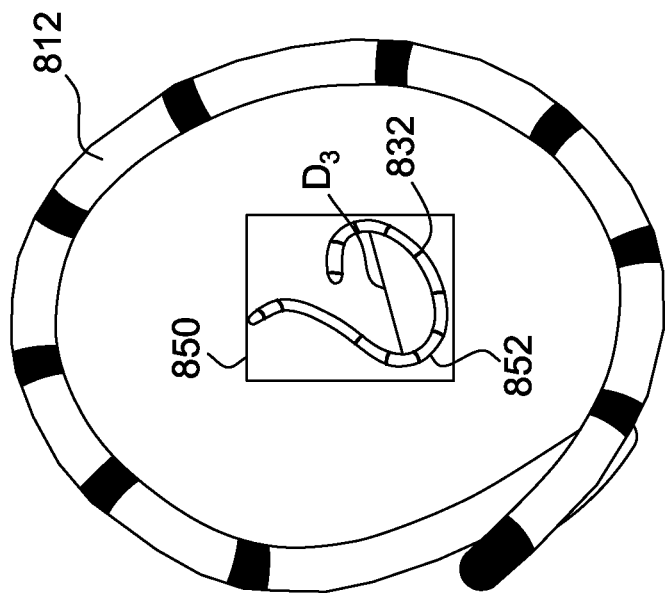
FIG. 8B is an example of a smoothed image of an elongate medical device according to the present disclosure.
Figure 8A:
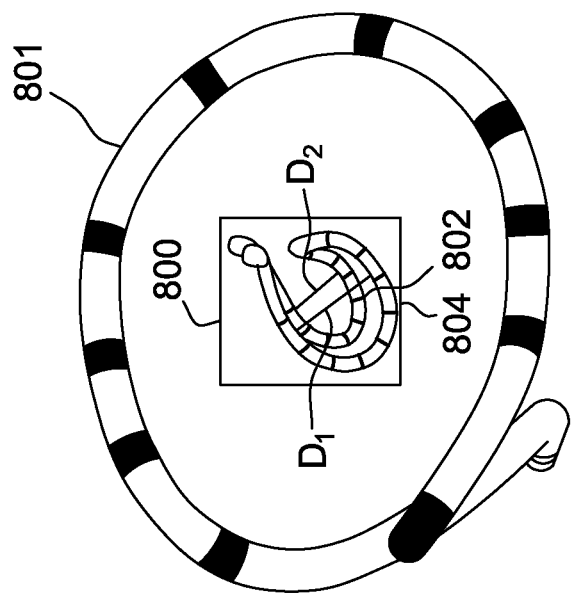
FIG. 8A is an example of a visual rendering of an elongate medical device using a previous method.

FIG. 8A is an example of a visual rendering 800 of an elongate medical device 801 using a previous method. Visual rendering 800 shows unevenly spaced electrodes 802, and substantially reduces a diameter $D_1$ of a curve 804 of medical device 801, resulting in a more elliptical than circular shape with a diameter $D_2$.

FIG. 8B is an example of a smoothed image 850 of an elongate medical device 812 according to the present disclosure. Smoothed image 850 is generated (step 614) using the algorithms and methods described herein, and may be displayed (step 616) on display device 44 (shown in FIG. 1). Smoothed image 850 features evenly spaced electrodes 832. Moreover, a diameter $D_3$ of a curve 852 of elongate medical device 812 is not reduced, producing a more circular shape.

The following discussions describe in further detail the solution to Equation (A), for curved splines (e.g., one-dimensional elongate medical devices) and planar catheters (e.g., two-dimensional elongate medical devices). All elongate medical devices, including catheters, both linear and circular, may be represented as 3D parametric curves with constant curve parameters. For straightened catheters, the curvature is zero, and for curved catheters, the curvature is non-zero. Smoothing performed by model construction system 14, such as an EnGuide™ smoothing system, may be expressed as a minimization of any warping required to fit measured electrode positions to a 3D curve of some unknown curvature. For any given curvature, the radial basis functions are well defined, and the weights on the resulting basis functions have an exact solution. Determination of the unknown curvature is then an optimization, minimizing the bending energy of the thin plate spline weights.

Curved Spline Implementation

A 3D curve may be represented by a Frenet moving frame as a differential parametric function of the curve. If the curvature, $\kappa$, and torsion, $\tau$, are constant for any distance on the arc, $\ell$, then the integration of the parametric function is equal the matrix exponential of the constant Frenet frame.

$$F = \begin{bmatrix} 0 & \kappa & 0 & 0 \\ -\kappa & 0 & \tau & 0 \\ 0 & -\tau & 0 & 0 \\ 1 & 0 & 0 & 0 \end{bmatrix} \ell$$

$$\Phi = \exp F(\kappa, \tau, \ell)$$

As matrix exponentials are not generally numerically efficient or accurate to compute, the following is applied:

$$\theta = \sqrt{\kappa^2 + \tau^2}$$

$$G(\kappa, \tau) = \begin{bmatrix} \frac{\kappa}{\theta} & 0 & \frac{\tau}{\theta} & 0 \\ 0 & 1 & 0 & 0 \\ -\frac{\tau}{\theta} & 0 & \frac{\kappa}{\theta} & 0 \\ 0 & 0 & 0 & 1 \end{bmatrix}$$

$$\Phi = (\kappa, \tau, \ell) = G(\kappa, \tau) \exp\left(\begin{bmatrix} 0 & \theta & 0 & 0 \\ -\theta & 0 & 0 & 0 \\ 0 & 0 & 0 & 0 \\ \frac{\kappa}{\theta} & 0 & \frac{\tau}{\theta} & 0 \end{bmatrix} \ell\right) G^T(\kappa, \tau)$$

After expanding the first several terms of the remaining matrix exponential, the following trigonometric series identities can be recognized:

$$\Phi = (\kappa, \tau, \ell) = G(\kappa, \tau) \begin{bmatrix} \cos(\theta\ell) & \sin(\theta\ell) & 0 & 0 \\ -\sin(\theta\ell) & \cos(\theta\ell) & 0 & 0 \\ 0 & 0 & 1 & 0 \\ \frac{\kappa}{\theta^2}\sin(\theta\ell) & \frac{\kappa}{\theta^2}(1-\cos(\theta\ell)) & \frac{\tau\ell}{\theta} & 1 \end{bmatrix} G^T(\kappa, \tau)$$

For the full $\Phi$ matrix, it is useful to leave the Givens rotations in the solution. The last row corresponds to the Cartesian coordinate of a point along the parametric curve and may be expressed with only the right Givens rotation.

$$P(\kappa, \tau, \ell) = \begin{bmatrix} \frac{\kappa}{\theta^2}\sin(\theta\ell) & \frac{\kappa}{\theta^2}(1-\cos(\theta\ell)) & \frac{\tau\ell}{\theta} & 1 \end{bmatrix} G^T(\kappa, \tau)$$

To establish the coordinate system of a catheter (e.g., a NavX™ coordinate system), a rigid-body transformation and a symmetric matrix describing the rotation-free NavX™ scaling or the general affine result of their composition may be composed as follows:

$$[x \ y \ z] = P(\kappa, \tau, \ell)\begin{bmatrix} Q \\ t^T \end{bmatrix}$$

$$S = P(\kappa, \tau, \ell)M$$

$$Q^T Q = I$$

$$S = S^T$$

Recognizing that the Givens rotation used in the matrix exponential and the curve-related constants may be included in the affine matrix, the location of a point (e.g., a position of an electrode 32) on a 3D curve may be expressed as follows:

$$M' = \begin{bmatrix} \frac{\kappa}{\theta^2} & 0 & 0 & 0 \\ 0 & -\frac{\kappa}{\theta^2} & 0 & 0 \\ 0 & 0 & \frac{\tau}{\theta} & 0 \\ 0 & \frac{\kappa}{\theta^2} & 0 & 1 \end{bmatrix} G^T M$$

$$[x \ y \ z] = [\sin(\theta\ell) \ \cos(\theta\ell) \ \ell \ 1] M'$$

where, for a given $x_i \in X$:

$$x_i = m_1^x \sin(\theta \ell_i) + m_2^x \cos(\theta \ell_i) + m_3^x \ell_i + m_4^x$$

It should be noted that, for a curved spline, $\kappa$ and $\tau$ fall out of the equation. In other words, the individual curve and torsion terms, although used to construct curvature $\theta$, do not independently affect the final location $x_i$. $\kappa$ and $\tau$ are included in the affine term, M, and the parametric form may be defined using the single non-linear parameter, $\theta$, and an affine linear term, M.

Including thin plate spline (TPS) terms, where $\psi(r)$ is the 1D radial basis function: $|r|^3$ $$x_i = m_1^x \sin(\theta\ell) + m_2^x \cos(\theta\ell) + m_3^x \ell_i + m_4^x + \sum_j w_j^x (\psi(\ell_i - \ell_j) - \lambda_i \delta_{ij})$$

with similar expressions for y and z.

In matrix form:

$$[X \ Y \ Z] = [\sin(\theta \mathcal{L}) \cos(\theta \mathcal{L}) \ \mathcal{L} \ 1^N \Psi][{}_W{}^{M'}]$$

For a given $\theta$ and $\lambda$, M' and W are exactly determined. The exact determination assumes orthogonality between the radial basis functions and the parametric catheter form, i.e., $W^T[\sin(\theta \mathcal{L})\cos(\theta \mathcal{L}) \ \mathcal{L} \ 1^N] = 0$ Iterate over $\theta$ to find the minimum $tr(W^T \Psi W)$. More specifically, assuming orthogonality between the radial basis functions and parametric catheter form, iterate over $\theta$ to find the minimum $\|\epsilon\|_F$ without the radial basis function.

Planar Catheter Implementation

A curved plane in space may be represented by the Frenet moving frame as a differential parametric function on the curve. If the curvature, $\kappa$, and torsion, r, are constant for any distance on the central arc, $\ell$, then the integration of the parametric function is equal the matrix exponential of the constant Frenet frame.

$$F = \begin{bmatrix} 0 & \kappa & 0 & 0 \\ -\kappa & 0 & \tau & 0 \\ 0 & -\tau & 0 & 0 \\ 1 & 0 & 0 & 0 \end{bmatrix} \ell$$

$$\Phi = \exp F(\kappa, \tau, \ell)$$

As matrix exponentials are not generally numerically efficient or accurate to compute, the following is applied:

$$\theta = \sqrt{\kappa^2 + \tau^2}$$

$$G(\kappa, \tau) = \begin{bmatrix} \frac{\kappa}{\theta} & 0 & \frac{\tau}{\theta} & 0 \\ 0 & 1 & 0 & 0 \\ -\frac{\tau}{\theta} & 0 & \frac{\kappa}{\theta} & 0 \\ 0 & 0 & 0 & 1 \end{bmatrix}$$

$$\Phi(\kappa, \tau, \ell) = G(\kappa, \tau) \exp\left(\begin{bmatrix} 0 & \theta & 0 & 0 \\ -\theta & 0 & 0 & 0 \\ 0 & 0 & 0 & 0 \\ \frac{\kappa}{\theta} & 0 & \frac{\tau}{\theta} & 0 \end{bmatrix} \ell\right) G^T(\kappa, \tau)$$

After expanding the first several terms of the remaining matrix exponential, the following trigonometric series identities can be recognized:

$$\Phi(\kappa, \tau, \ell) = G(\kappa, \tau) \begin{bmatrix} \cos(\theta\ell) & \sin(\theta\ell) & 0 & 0 \\ -\sin(\theta\ell) & \cos(\theta\ell) & 0 & 0 \\ 0 & 0 & 1 & 0 \\ \frac{\kappa}{\theta^2}\sin(\theta\ell) & \frac{\kappa}{\theta^2}(1-\cos(\theta\ell)) & \frac{\tau\ell}{\theta} & 1 \end{bmatrix} G^T(\kappa, \tau)$$

For the full $\Phi$ matrix, it is useful to leave the Givens rotations in the solution. The last row corresponds to the Cartesian coordinate of a point (e.g., a position of an electrode 32) along the curve and may be expressed with only the right Givens rotation.

In order to preserve arclengths for paths spread some distance, $u_2$, from the central axis (e.g., central axis 422), a normalization must be applied so that for some arclength, $u_1$, spaced $u_2$ from the central axis, the Frenet frame should be computed with $\ell$ as follows:

$$\ell = \frac{u_1}{\sqrt{1 + \tau^2 u_2^2}}$$

This is simply a correction to compute the length of a leg that preserves the length of a hypotenuse.

A point is then located on the plane by multiplying by the Frenet frame:

$$P(\kappa, \tau, u_1, u_2) = [0 \ u_2 \ 0 \ 1] \Phi\left(\kappa, \tau, \frac{u_1}{\sqrt{1+\tau^2 u_2^2}}\right)$$

Substituting:

$$P(\kappa, \tau, u_1, u_2) = [0 \ u_2 \ 0 \ 1] \begin{bmatrix} \cos(\theta\ell) & \sin(\theta\ell) & 0 & 0 \\ -\sin(\theta\ell) & \cos(\theta\ell) & 0 & 0 \\ 0 & 0 & 1 & 0 \\ \frac{\kappa}{\theta^2}\sin(\theta\ell) & \frac{\kappa}{\theta^2}(1-\cos(\theta\ell)) & \frac{\tau\ell}{\theta} & 1 \end{bmatrix} G^T(\kappa, \tau)$$

The left Givens rotation does not affect the point being projected.

$$[0 \ u_2 \ 0 \ 1]G(\kappa,\tau) = [0 \ u_2 \ 0 \ 1]$$

$$P(\kappa, \tau, u_1, u_2) = [0 \ u_2 \ 0 \ 1] \begin{bmatrix} \cos(\theta\ell) & \sin(\theta\ell) & 0 & 0 \\ -\sin(\theta\ell) & \cos(\theta\ell) & 0 & 0 \\ 0 & 0 & 1 & 0 \\ \frac{\kappa}{\theta^2}\sin(\theta\ell) & \frac{\kappa}{\theta^2}(1-\cos(\theta\ell)) & \frac{\tau\ell}{\theta} & 1 \end{bmatrix} G^T(\kappa, \tau)$$

Projecting the point by the central part of the Frenet frame yields:

$$P(\kappa, \tau, u_1, u_2) = \left[ \left(\frac{\kappa}{\theta^2} - u_2\right)\sin(\theta\ell) \ \ \frac{\kappa}{\theta^2} + \left(u_2 - \frac{\kappa}{\theta^2}\right)\cos(\theta\ell) \ \ \frac{\tau\ell}{\theta} \ \ 1 \right] G^T(\kappa, \tau)$$

To establish the coordinate system of a catheter (e.g., a NavX™ coordinate system), a rigid-body transformation and a symmetric matrix describing the rotation-free NavX™ scaling or the general affine result of their composition may be composed:

$$[x \ y \ z] = P(\kappa, \tau, u_1, u_2) \begin{bmatrix} Q \\ t^T \end{bmatrix} S = P(\kappa, \tau, u_1, u_2) M$$

$$Q^T Q = I$$

$$S = S^T$$

Recognizing that the Givens rotation used in the matrix exponential and some curve-related constants may be included in the affine matrix, the location of a point on a 3D curve as follows can be expressed as follows:

$$P(\kappa, \tau, u_1, u_2) = \left[ \left(u_2 - \frac{\kappa}{\theta^2}\right)\sin(\theta\ell) \ \ \left(u_2 - \frac{\kappa}{\theta^2}\right)\cos(\theta\ell) \ \ \ell \ \ 1 \right] \begin{bmatrix} -1 & 0 & 0 & 0 \\ 0 & 1 & 0 & 0 \\ 0 & 0 & \frac{\tau}{\theta} & 0 \\ 0 & \frac{\kappa}{\theta^2} & 0 & 1 \end{bmatrix} G^T(\kappa, \tau)$$

$$M' = \begin{bmatrix} -1 & 0 & 0 & 0 \\ 0 & 1 & 0 & 0 \\ 0 & 0 & \frac{\tau}{\theta} & 0 \\ 0 & \frac{\kappa}{\theta^2} & 0 & 1 \end{bmatrix} G^T M$$

$$[x \ y \ z] = \left[ \left(u_2 - \frac{\kappa}{\theta^2}\right)\sin(\theta\ell) \ \ \left(u_2 - \frac{\kappa}{\theta^2}\right)\cos(\theta\ell) \ \ \ell \ \ 1 \right] M'$$

where, for a given $x_i \in X$:

$$x_i = m_1^x \left(u_2 - \frac{\kappa}{\theta^2}\right)\sin(\theta\ell) + m_2^x\left(u_2 - \frac{\kappa}{\theta^2}\right)\cos(\theta\ell) + m_3^x \ell_i + m_4^x$$

Including TPS terms, where (r) is the 2D radial basis function, $r^2 \ln(r)$:

$$x_i = m_1^x\left(u_2 - \frac{\kappa}{\theta^2}\right)\sin(\theta\ell) + m_2^x\left(u_2 - \frac{\kappa}{\theta^2}\right)\cos(\theta\ell) + m_3^x \ell_i + m_4^x + \sum_j w_j^x(\psi(|[u_1 \ u_2]_i - [u_1 \ u_2]_j|) - \lambda_i \delta_{ij})$$

with similar expressions for y and z.

In matrix form:

$$[X \ Y \ Z] = \left[ \left(\mathcal{U}_{:,2} - \frac{1^N \kappa}{\theta^2}\right) \circ \sin(\theta\mathcal{L}) \ \ \left(\mathcal{U}_{:,2} - \frac{1^N \kappa}{\theta^2}\right) \circ \cos(\theta\mathcal{L}) \ \ \mathcal{L} \ \ 1^N \ \ \Psi \right] \begin{bmatrix} M' \\ W \end{bmatrix}$$

For a given κ, τ, and λ, M' and W are exactly determined. The exact determination assumes orthogonality between the radial basis functions and the parametric catheter form, i.e., $W^T[\sin(\theta\mathcal{L})\cos(\theta\mathcal{L}) \ \mathcal{L} \ 1^N] = 0$ Iterate over κ, τ to find the least-squares fit without the radial basis functions. Once found, solve for M' and W as in TPS.

It should be understood that the smoothing methods described herein may also be implemented for additional medical devices, including balloon catheters and/or 3D catheters. In such embodiments, the algorithms are adjusted accordingly.

It should be understood that model construction system 14, and particularly processing apparatus 16, as described above, may include conventional processing apparatus known in the art, capable of executing pre-programmed instructions stored in an associated memory, all performing in accordance with the functionality described herein. It is contemplated that the methods described herein, including without limitation the method steps of embodiments of the invention, will be programmed in some embodiments, with the resulting software being stored in an associated memory and where so described, may also constitute the means for performing such methods. Implementation of the invention, in software, in view of the foregoing enabling description, would require no more than routine application of programming skills by one of ordinary skill in the art. Such a system may further be of the type having both ROM, RAM, a combination of non-volatile and volatile (modifiable)

memory so that the software can be stored and yet allow storage and processing of dynamically produced data and/or signals.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A system for generating an image of an elongate medical device located within a body, the elongate medical device including a plurality of position sensors, the system comprising:
a computer-based model construction system comprising a processing apparatus and a memory device, the computer-based model construction system configured to be coupled to the elongate medical device and configured to acquire a set of measured data points corresponding to respective positions of the plurality of position sensors, the computer-based model construction system further configured to:
establish a coordinate system associated with the elongate medical device;
calculate a respective coordinate in the coordinate system for each of the plurality of position sensors;
calculate a set of estimated parameters describing the elongate medical device as a geometry having a constant curvature value and a constant torsion value, the set of estimated parameters including a curve parameter, wherein the curve parameter squared is the sum of the curvature value squared and the torsion value squared, and wherein the set of estimated parameters defines an estimated position for each of the plurality of position sensors;
calculate a measurement error for each of the plurality of position sensors based at least in part on a respective stiffness parameter, wherein the stiffness parameter for a position sensor defines an amount of permitted variation in the measured data point for that position sensor;
compute smoothed data points for the plurality of position sensors based on (i) a function of the set of estimated parameters and the respective coordinates of each of the plurality of position sensors, and (ii) a fraction of the measurement error;
generate an image of the elongate medical device using the smoothed data points; and
display the generated image.

2. The system of claim 1, wherein the elongate medical device is a planar medical device, and wherein the respective coordinate of each of the plurality of position sensors is a two-dimensional coordinate in a plane defined by a surface of the elongate medical device, with a first term of the two-dimensional coordinate specifying a displacement of a position sensor along a central axis of the plane and with a second term of the two-dimensional coordinate specifying a displacement of the position sensor perpendicular to the central axis of the plane.

3. The system of claim 1, wherein the elongate medical device is a curved or linear medical device, and wherein the respective coordinate of each of the plurality of position sensors is a scalar representing an arclength between a distal-most position sensor of the plurality of position sensors and each corresponding position sensor along the elongate medical device.

4. The system of claim 1, wherein the set of estimated parameters further includes an affine transformation term.

5. The system of claim 1, wherein the coordinate system is a cylindrical coordinate system.

6. The system of claim 1, wherein the set of estimated parameters further includes at least one of: a number of position sensors along a surface of the elongate medical device, a distance between adjacent position sensors, and a length of the elongate medical device.

7. The system of claim 1, wherein the measurement error represents a linear combination of a set of radial basis functions.

8. The system of claim 1, wherein the computer-based model construction system is further configured to calculate the set of estimated parameters as a non-linear least-squares solution to the set of measured data points.

9. The system of claim 1, wherein the elongate medical device is one-dimensional and the geometry is a curve.

10. The system of claim 1, wherein the elongate medical device is two-dimensional and the geometry is a plane.

11. A computer-implemented method of generating an image of an elongate medical device located within a body, the elongate medical device including a plurality of position sensors, the method comprising:
acquiring a set of measured data points corresponding to respective positions of the plurality of position sensors;
establishing a coordinate system associated with the elongate medical device;
calculating a respective coordinate in the coordinate system for each of the plurality of position sensors;
calculating a set of estimated parameters describing the elongate medical device as a geometry having a constant curvature value and a constant torsion value, the set of estimated including a curve parameter, wherein the curve parameter squared is the sum of the curvature value squared and the torsion value squared, and wherein the set of estimated parameters defines an estimated position for each of the plurality of position sensors;

calculating a measurement error for each of the plurality of position sensors based at least in part on a respective stiffness parameter, wherein the stiffness parameter for a position sensor defines an amount of permitted variation in the measured data point for that position sensor;

computing smoothed data points for the plurality of position sensors based on (i) a function of the set of estimated parameters and the respective coordinates of each of the plurality of position sensors, and (ii) a fraction of the measurement error;

generating an image of the elongate medical device using the smoothed data points; and displaying the generated image.

12. The method of claim 11, wherein the elongate medical device is a planar medical device, and wherein calculating a respective coordinate comprises calculating the respective coordinate of each of the plurality of position sensors as a two-dimensional coordinate in a plane defined by a surface of the elongate medical device, with a first term of the two-dimensional coordinate specifying a displacement of a position sensor along a central axis of the plane and with a second term of the two-dimensional coordinate specifying a displacement of the position sensor perpendicular to the central axis of the plane.

13. The method of claim 11, wherein the elongate medical device is a curved or linear medical device, and wherein calculating a respective coordinate comprises calculating the respective coordinate of each of the plurality of position sensors as a scalar representing an arclength between a distal-most position sensor of the plurality of position sensors and each corresponding position sensor along the elongate medical device.

14. The method of claim 11, wherein establishing a coordinate system associated with the elongate medical device comprises establish a cylindrical coordinate system associated with the elongate medical device.

15. The method of claim 11, wherein calculating a set of estimated parameters comprises calculating the set of estimated parameters as a non-linear least-squares solution to the set of measured data points.

16. The method of claim 11, wherein the elongate medical device is one-dimensional and the geometry is a curve.

17. The method of claim 11, wherein the elongate medical device is two-dimensional and the geometry is a plane.

18. A processing apparatus for generating an image of an elongate medical device located within a body, the elongate medical device including a plurality of position sensors, the processing apparatus configured to:

acquire a set of measured data points corresponding to respective positions of the plurality of position sensors;

establish a coordinate system associated with the elongate medical device;

calculate a respective coordinate in the coordinate system for each of the plurality of position sensors;

calculate a set of estimated parameters describing the elongate medical device as a geometry having a constant curvature value and a constant torsion value, the set of estimated parameters including a curve parameter, wherein the curve parameter squared is the sum of the curvature value squared and the torsion value squared, and wherein the set of estimated parameters defines an estimated position for each of the plurality of position sensors;

calculate a measurement error for each of the plurality of position sensors based at least in part on a respective stiffness parameter, wherein the stiffness parameter for a position sensor defines an amount of permitted variation in the measured data point for that position sensor;

compute smoothed data points for the plurality of position sensors based on (i) a function of the set of estimated parameters and the respective coordinates of each of the plurality of position sensors, and (ii) a fraction of the measurement error;

generate an image of the elongate medical device using the smoothed data points; and display the generated image.

19. The processing apparatus of claim 18, wherein the set of estimated parameters further includes at least one of: a number of position sensors along a surface of the elongate medical device, a distance between adjacent position sensors, and a length of the elongate medical device.

20. The processing apparatus of claim 18, wherein the measurement error represents a linear combination of a set of radial basis functions.

* * * * *